(12) United States Patent
Yoda et al.

(10) Patent No.: US 10,006,570 B2
(45) Date of Patent: Jun. 26, 2018

(54) PIPE JOINT

(71) Applicant: JUNKOSHA INC., Kasama-shi, Ibaraki (JP)

(72) Inventors: Keiji Yoda, Kasama (JP); Hiroji Oda, Kasama (JP)

(73) Assignee: JUNKOSHA INC., Kasama-Shi, Ibaraki (JP)

( * ) Notice: Subject to any disclaimer, the term of this patent is extended or adjusted under 35 U.S.C. 154(b) by 211 days.

(21) Appl. No.: 14/900,708

(22) PCT Filed: Jun. 20, 2014

(86) PCT No.: PCT/JP2014/066484
§ 371 (c)(1),
(2) Date: Dec. 22, 2015

(87) PCT Pub. No.: WO2015/001993
PCT Pub. Date: Jan. 8, 2015

(65) Prior Publication Data
US 2016/0131286 A1   May 12, 2016

(30) Foreign Application Priority Data

Jul. 5, 2013  (JP) .................................. 2013-142120
Dec. 5, 2013  (JP) .................................. 2013-252561

(51) Int. Cl.
| | |
|---|---|
| *F16L 19/08* | (2006.01) |
| *F16L 19/06* | (2006.01) |
| *A61M 39/10* | (2006.01) |

(52) U.S. Cl.
CPC ........... *F16L 19/086* (2013.01); *F16L 19/061* (2013.01); *A61M 2039/1038* (2013.01); *A61M 2039/1066* (2013.01); *F16L 2201/44* (2013.01)

(58) Field of Classification Search
CPC ... F16L 19/086; F16L 19/061; F16L 2201/44; F16L 37/091; F16L 15/06;
(Continued)

(56) References Cited

U.S. PATENT DOCUMENTS

| | | | | |
|---|---|---|---|---|
| 4,900,068 A | * | 2/1990 | Law ...................... | F16L 33/222 285/139.2 |
| 5,051,541 A | * | 9/1991 | Bawa ..................... | H02G 3/088 285/151.1 X |

(Continued)

FOREIGN PATENT DOCUMENTS

| | | |
|---|---|---|
| DE | 3731222 A1 | 4/1989 |
| EP | 1607670 A1 | 12/2005 |

(Continued)

OTHER PUBLICATIONS

Jan. 30, 2017, European Search Report for related EP application No. 14819289.1.

*Primary Examiner* — Greg Binda
*Assistant Examiner* — Zachary T Dragicevich
(74) *Attorney, Agent, or Firm* — Paratus Law Group, PLLC

(57) ABSTRACT

A pipe joint includes a joint main body, a cap nut, a sleeve, an insertion groove between a pipe body mounting section and an external thread section of the joint main body, and an elastic member disposed in the insertion groove. When the external thread section and an internal thread section of the cap nut are screwed, the end face of the distal end side of the sleeve comes into contact with one end face of the elastic member to compress the elastic member, and the elastic member presses, with a self-repulsion force, the end face of the distal end side of the sleeve in the axial direction. Then, an inner circumferential surface of a proximal end side of the sleeve compresses the pipe body in a radial direction of the (Continued)

pipe body through a reaction force received from a fitting surface of the cap nut.

7 Claims, 5 Drawing Sheets

(58) Field of Classification Search
CPC .. A61M 2039/1066; A61M 2039/1038; H02G 3/083; H02G 3/088; H02G 3/0616
USPC ... 285/141.1, 149.1, 151.1, 319, 331, 139.1, 285/139.2
See application file for complete search history.

(56) References Cited

U.S. PATENT DOCUMENTS

| | | | |
|---|---|---|---|
| 5,405,172 A * | 4/1995 | Mullen, Jr. | F16L 19/08 285/139.1 X |
| 6,642,451 B1 * | 11/2003 | Gretz | F16L 37/091 |
| 6,767,032 B1 * | 7/2004 | Gretz | F16L 37/091 285/151.1 X |
| 2006/0219437 A1 * | 10/2006 | Chiu | H02G 3/088 174/653 |
| 2009/0224536 A1 | 9/2009 | Fukushima et al. | |

FOREIGN PATENT DOCUMENTS

| | | |
|---|---|---|
| EP | 2233814 A1 | 2/2010 |
| JP | 64-038385 U1 | 3/1989 |
| JP | 2007-333176 | 12/2007 |
| JP | 2011-52772 | 3/2011 |
| JP | 2011-69484 | 4/2011 |
| JP | 3175395 U | 5/2012 |
| WO | WO2007/004343 A1 | 1/2007 |
| WO | WO2007/029068 A1 | 3/2007 |
| WO | WO2011/027766 A1 | 3/2011 |
| WO | WO2011/037267 A1 | 3/2011 |
| WO | WO2013/058358 A1 | 4/2013 |

* cited by examiner

400

PIPE JOINT

CROSS REFERENCE TO PRIOR APPLICATION

This application is a National Stage Patent Application of PCT International Patent Application No. PCT/JP2014/066484 (filed on Jun. 20, 2014) under 35 U.S.C. § 371, which claims priority to Japanese Patent Application Nos. 2013-252561 (filed on Dec. 5, 2013) and 2013-142120 (filed on Jul. 5, 2013), which are all hereby incorporated by reference in their entirety.

TECHNICAL FIELD

The present invention relates to a pipe joint that is used in connection between a pipe body, such as a hose, and equipment or the like.

BACKGROUND ART

In general, a pipe joint which connects a pipe body, such as a hose, and equipment or the like, needs to have high sealability in a joint section with respect to a fluid flowing inside the pipe body. As such a pipe joint in the related art, Patent Document 1 discloses a pipe joint that has a structure in which a synthetic resin pipe is connected to a metal joint main body formed to have an inner tapered surface in a receiving-side opening through a cap nut having an inner tapered surface and a sleeve is interposed in a space formed by the two inner tapered surfaces and an outer circumferential surface of a connection-side end of the synthetic resin pipe, and that has a seal structure in which an annular groove is formed in the inner circumferential surface of the sleeve and an O-ring is interposed.

CITATION LIST

Patent Document

[Patent Document 1] JP-UM-A-64-38385

SUMMARY OF INVENTION

Problems to be Solved by Invention

In the pipe joint in the related art described above, the sleeve is reduced in diameter by approach movement of an inclined surface facing the cap nut when the cap nut is screwed to the joint main body, and thereby the inner circumferential surface of the sleeve comes into pressing contact with the outer circumferential surface of the pipe body such that sealability is secured. However, for example, in a case where a fluid or the like, which contains a medicinal substance, is transferred in medical equipment or the like, a pipe joint for connecting the medical equipment and the pipe, through which the fluid is transferred, is used. The pipe joint for such a use needs to have still higher sealability from the properties of the fluid flowing inside the pipe body, whereas a certain number of cycles of maintenance in which hot water or the like is caused to flow inside the pipe body in a state of being connected to the pipe joint and to perform disinfection or the like are often performed. Accordingly, in such an use, a temperature cycle in which hot water having a temperature of approximately 100° C. flows inside the pipe body which is normally disposed at normal temperature is repeatedly performed, and as a result, a pressing-contact portion of the pipe joint by the sleeve is irreversibly deformed in a distal end portion of the pipe body and a thickness size of the pressing-contact portion is decreased, and airtightness (liquid-tightness) with the pipe body is damaged in some cases. Therefore, in the related art, problems arise in that leakage occurs by the temperature cycle for a short period of time and there is a need to perform replacement operation of the joint components and the pipe body. For example, the pipe joint disclosed in Patent Document 1 is unlikely to cope with such deformation of the pipe body and is insufficient in terms of durability under a severe temperature cycle environment in which a temperature on the high temperature side described above is significantly changed.

The present invention is provided in consideration of such problems, and an object thereof is to provide a pipe joint in which high sealability is obtained and sufficient durability is obtained even under a temperature cycle environment of a temperature of approximate 100° C. from normal temperature in a structure.

Means for Solving the Problems

The present inventors make a close study of the structure of the pipe joint in which sufficient durability is obtained even under such a temperature cycle environment described above, and as a result an elastic member having substantially a ring shape, which corresponds to an end face of a distal end side of a sleeve, is disposed in the insertion groove provided at a portion in which a distal end of a pipe body of the joint main body is inserted, and after the pipe body is mounted, the elastic member presses, with the self-repulsion force, the end face of the distal end side of the sleeve in the axial direction. In this manner, the inner circumferential surface of the proximal end side of the sleeve compresses the pipe body in the radial direction, and thereby it is possible to maintain sufficient airtightness (liquid-tightness) even with respect to the deformation of the pipe body in the structure for obtaining high sealability. A pipe joint, in which high sealability is obtained and highly greater durability is obtained even under a severe temperature cycle environment of a temperature of approximately 100° C. from normal temperature than that in the pipe joint in the related art, is obtained.

In order to achieve the above object, a pipe joint of the present invention comprising:

a joint main body that has a flow path inside thereof and that comprises a pipe body mounting section on an outer side of which a pipe body having substantially a cylindrical shape is mounted and an external thread section;

a cap nut having an inner circumferential surface including an internal thread section which is screwed to the external thread section of the joint main body; and a sleeve having substantially a cylindrical shape having an outer diameter capable of coming into sliding contact with the inner circumferential surface of the cap nut, and the pipe joint further comprises:

an insertion groove which is formed between the pipe body mounting section and the external thread section of the joint main body and in which a distal end of the pipe body is inserted; and an elastic member which is disposed in the insertion groove and which comprises a synthetic resin formed to have substantially a ring shape, the elastic member facing to an end face of a distal end side of the sleeve, in which in response to the external thread section of the joint main body and the internal thread section of the cap nut being screwed, the end face of the distal end side of the sleeve comes into contact with one end face of the elastic member in an axial direction thereof to compress the elastic member, and the elastic member presses, with a self-repulsion force, the end face of the distal end side of the sleeve in the axial direction, so that an inner circumferential surface of a proximal end side of the sleeve compresses the pipe body in a radial direction of the pipe body through a reaction force received from a fitting surface of the cap nut, and the elastic member itself compresses the pipe body in the radial direction of the pipe body.

A durometer hardness of the elastic member may be preferably 40A to 50A. The pipe joint may further comprises a sleeve mounting elastic member having substantially a ring shape, which is mounted on the inner circumferential surface of the proximal end side of the sleeve, in which the inner circumferential surface of the proximal end side of the sleeve compresses the pipe body in the radial direction of the pipe body through the sleeve mounting elastic member. Furthermore, the sleeve may preferably include at least one notch extending from one end portion in the axial direction.

BRIEF DESCRIPTION OF DRAWINGS

FIG. 4A is an elevation view (front view), FIG. 4B is a back elevation view (rear view), and FIG. 4C is a side view.

EMBODIMENTS FOR CARRYING OUT THE INVENTION

The present invention is not limited to embodiments in the following description, and every combination of features described in the embodiments is not essential for realization of the present invention.

Figure 1:
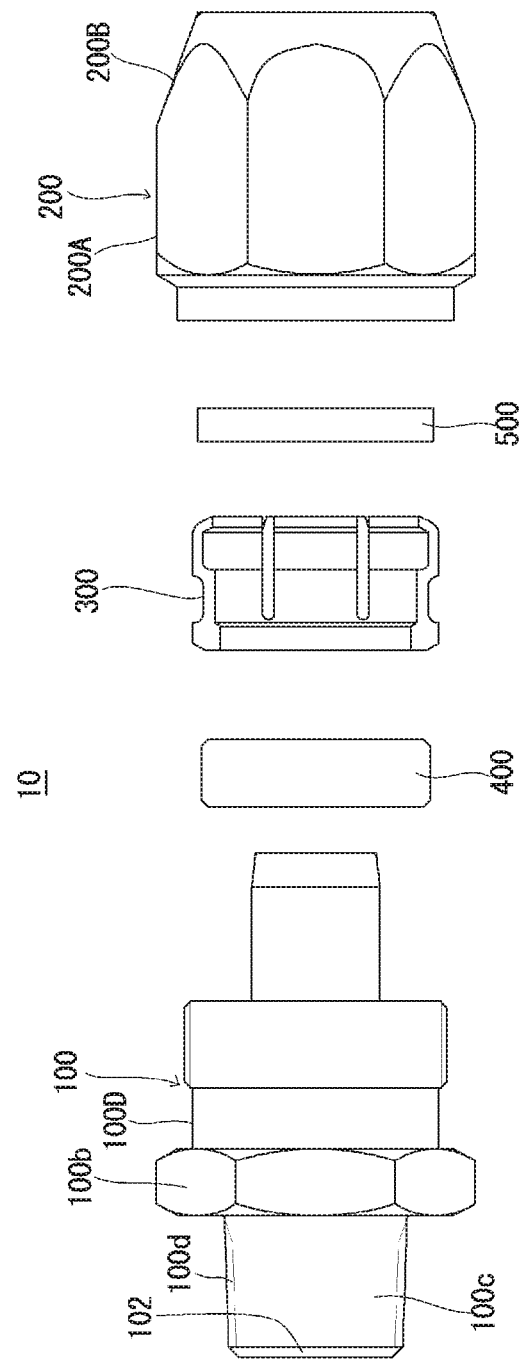
FIG. 1 is an exploded view of a pipe joint of an embodiment of the present invention.
Figure 2:
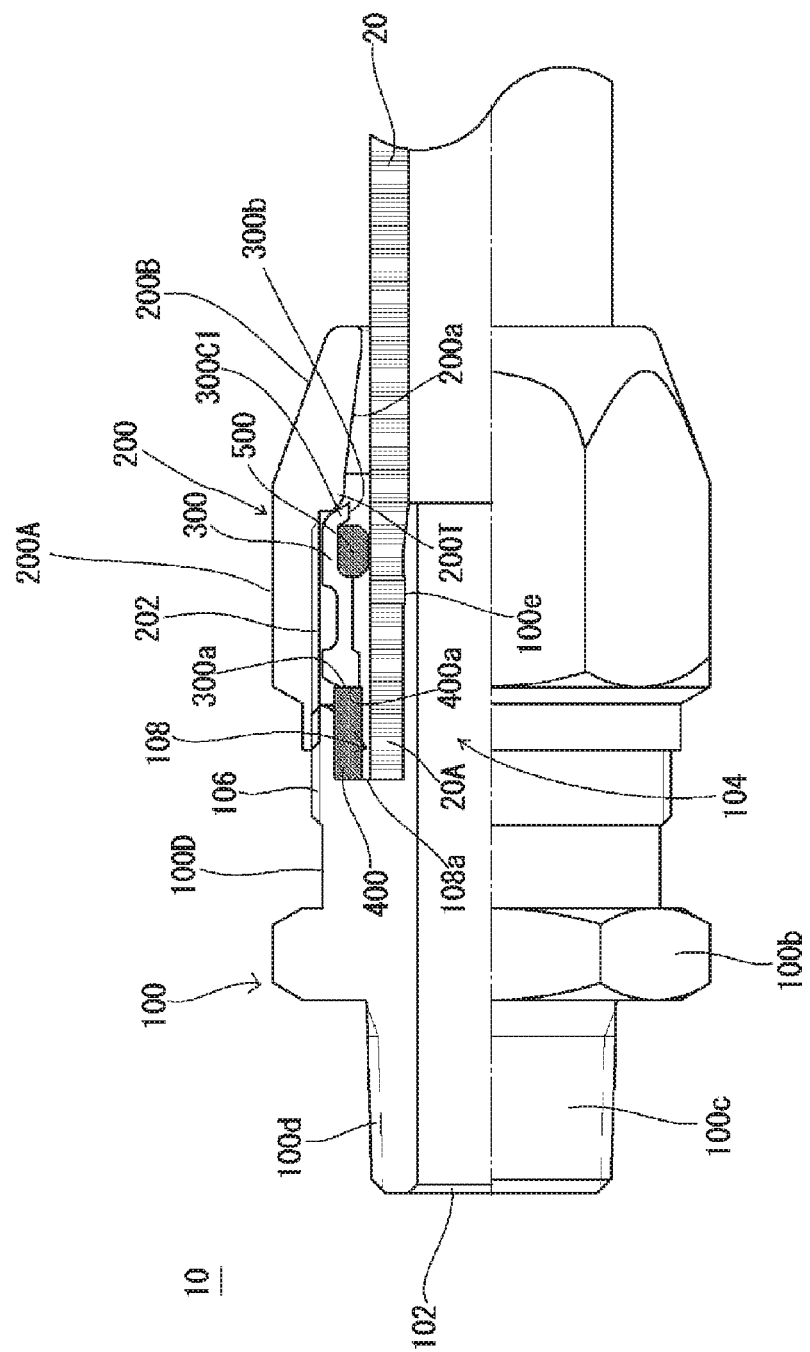
FIG. 2 is a partially cutaway sectional view illustrating a state in which a cup nut has yet to be screwed to a joint main body in the pipe joint of the embodiment of the present invention.
Figure 3:
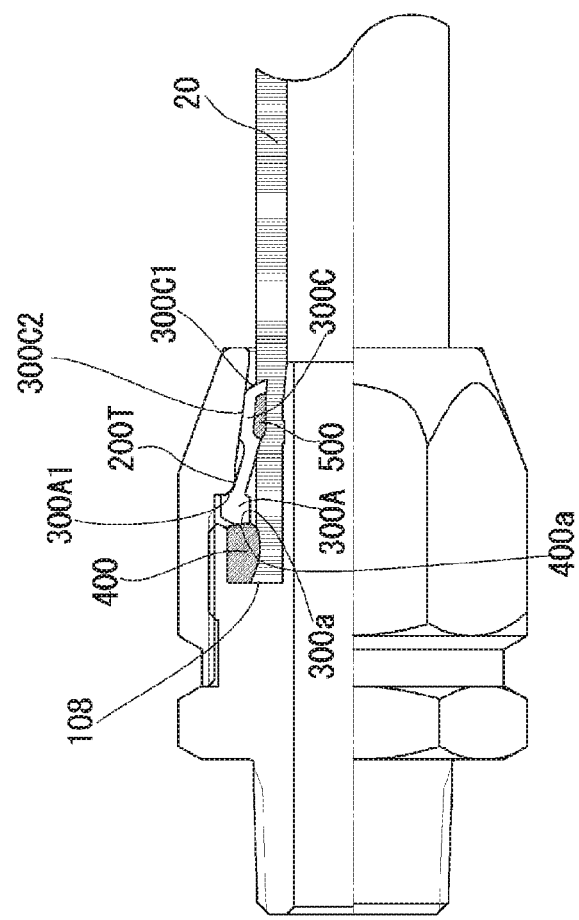
FIG. 3 is a partially cutaway sectional view illustrating a state in which the cap nut is screwed to the joint main body in the pipe joint of the embodiment of the present invention.
Figure 4:
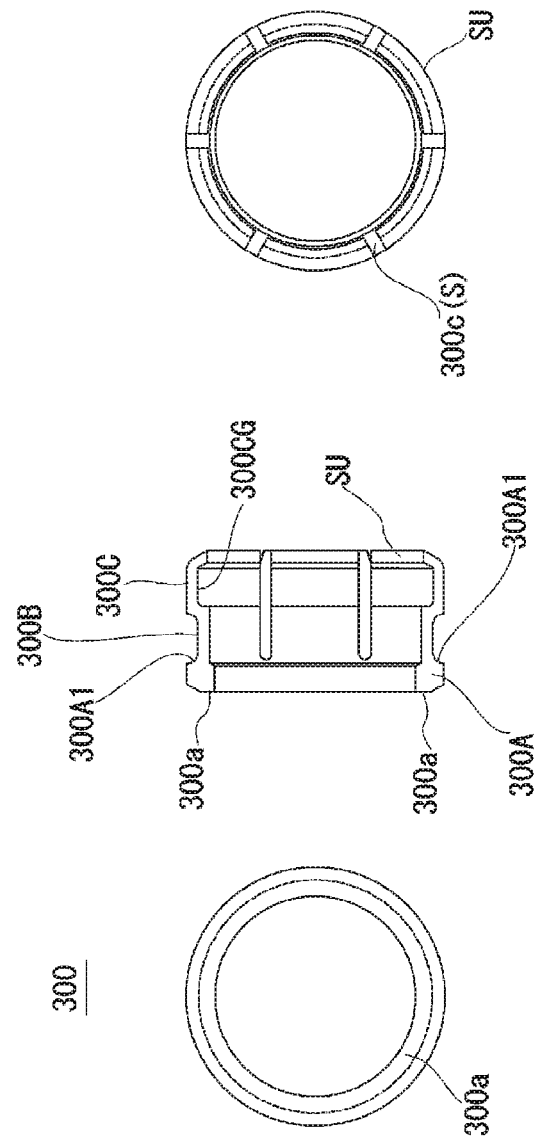
FIGS. 4A to 4C are views illustrating a sleeve in the pipe joint of the embodiment of the present invention.
Figure 5:
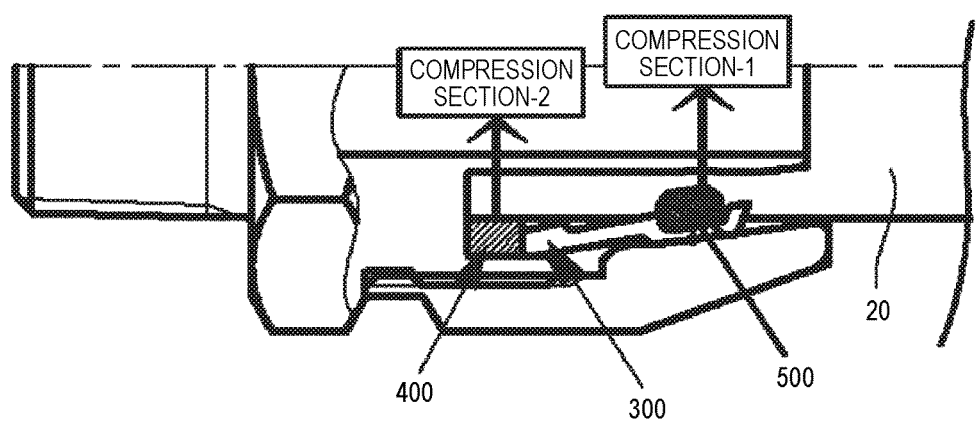
FIG. 5 is an enlarged view of a part in FIG. 3 and illustrating principles of two compressional operations by the pipe joint of the embodiment of the present invention.
Figure 6:
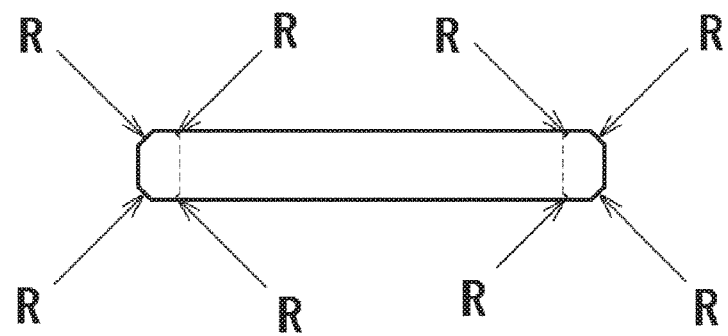
FIG. 6 is an elevation view of an elastic member in the pipe joint of the embodiment of the present invention, and illustrating a chamfering configuration of the elastic member.

FIG. 1 is an exploded view of a pipe joint of an embodiment of the present invention. FIG. 2 is a partially cutaway sectional view illustrating a state in which a cup nut has yet to be screwed to a joint main body. FIG. 3 is a partially cutaway sectional view illustrating a state in which the cap nut is screwed to the joint main. FIGS. 4A to 4C are views illustrating a sleeve; FIG. 4A is an elevation view (front view), FIG. 4B is a back elevation view (rear view), and FIG. 4C is a side view. FIG. 5 is an enlarged view of a part in FIG. 3, illustrating principles of two compressional operations by the pipe joint of the embodiment of the present invention, illustrating only a half of the pipe joint in an axial direction in the state in which the cap nut is screwed to the joint main body. FIG. 6 is an elevation view of an elastic member in the pipe joint of the embodiment of the present invention, and illustrating a chamfering configuration of the elastic member.

A pipe joint of the present embodiment is a joint which can be realized in the field and, basically, it is possible for a joint builder to perform mounting of a pipe member to a joint main body, or the like, by hand, other than fastening a nut by a tool, or the like. As illustrated in FIG. 1, FIG. 2, and FIG. 5, a pipe joint 10 of the present embodiment includes a flow path 102 inside thereof, a joint main body 100 including a pipe body mounting section 104 on an outer side of which a pipe body 20 having substantially a cylindrical shape is mounted and an external thread section 106, a cup nut 200 including an internal thread section 202 which is screwed to the external thread section 106 of the joint main body 100, and a sleeve 300 having substantially a cylindrical shape, which is fitted to the inside of the cap nut 200. An insertion groove 108, to which a distal end 20A of the pipe body 20 is inserted, and a ring-shaped elastic member 400 composed of a synthetic resin, which is disposed in the insertion groove 108 and faces to an end face 300a of a distal end side of the sleeve 300, are positioned between the pipe body mounting section 104 and the external thread section 106 of the joint main body 100. When the external thread section 106 of the joint main body 100 and the internal thread section 202 of the cap nut 200 are screwed, the end face 300a of the distal end side of the sleeve 300 comes into contact with one end face 400a of the elastic member 400 in the axial direction so as to compress the elastic member, then the elastic member 400 exerts a self-repulsion force and presses the end face 300a of the distal end side of the sleeve 300 is pressed in the axial direction, and thereby an inner circumferential surface 300b of a proximal end face of the sleeve 300 compresses the pipe body 20 in its radial direction, with a reaction force against a fitting surface 200a of the cap nut 200. At this time, the compressed elastic member 400 is tightly pressed to come into close contact with a wall surface of the insertion groove 108 and with the outer circumferential surface of the pipe body 20, and thereby it is possible to cause the self-repulsion force of the elastic member 400 to be stable and to be effectively applied to the sleeve 300. Specifically, as illustrated in FIG. 5, in the pipe joint of the present embodiment, the inner circumferential surface 300b of the proximal end side of the sleeve 300 not only compresses the pipe body 20 in its radial direction (compression section-1), with the reaction force against the fitting surface 200a of the cap nut 200, but also the elastic member 400 itself compresses the pipe body 20 in its radial direction (compression section-2) along with the compression (compression section-1) by the sleeve 300. According to such a configuration, although a distal end portion of the pipe body 20 starts to irreversibly deform under a severe temperature cycle environment, the elastic member 400 continues to press the sleeve 300 in the axial direction. As a result, since the inner circumferential surface 300b of the proximal end side of the sleeve 300 compresses the distal end portion of the pipe body 20, with a reaction force against a fitting surface 200a of the cap nut 200, and the elastic member 400 itself compresses the pipe body 20 in the radial direction, the pipe joint 10 has an airtight (liquid-tight) structure with the pipe body 20 which is unlikely to be impaired. In addition, as illustrated in FIG. 4, the sleeve 300 includes a plurality of notches 300c which extend from one end portion in its axial direction such that, when the external thread section 106 of the joint main body 100 and the internal thread section 202 of the cap nut 200 are screwed, intervals of the notches 300c are narrowed and the diameter of the sleeve 300 is reduced. In this manner, the inner circumferential surface 300b of the proximal end side of the sleeve 300 compresses the pipe body 20 in the radial direction, which results in high sealability. Further, an annular groove is formed in the inner circumferential surface 300b of the proximal end side of the sleeve 300 and a sleeve mounting elastic member 500 having substantial ring shape is mounted in the groove. Thus, the inner circumferential surface 300b of the proximal end side of the sleeve 300 compresses the pipe body 20 in the radial direction through the sleeve mounting elastic member 500. In this manner, with the sleeve mounting elastic member 500, in addition to the elastic member 400 described above, it is possible to further improve the sealability.

Hereinafter, the respective members of the pipe joint 10 of the present embodiment will be described in detail. The joint main body 100 is formed to have substantially a cylindrical shape with a given inner diameter and a given length through which a fluid passes. A spanner receiving protrusion ring 100b is formed on an hexagonal outer circumferential surface at the center portion of the joint main body, and an attaching cylindrical section 100c having the outer circumferential surface, on which screw threads 100d that are screwed to a cylindrical opening of medical equipment (not illustrated) through which a fluid including a medicinal substance, or the like, flows in and out, is formed on the left side from the protrusion ring 100b in FIG. 2 and FIG. 3. The external thread section 106 is formed on an outer circumferential surface of a cylindrical section 100D on the right side from the protrusion ring 100b on the drawings. In addition, the pipe body mounting section 104 is formed as a cylindrical section for inserting a pipe body, in the cylindrical section 100D, through the annular insertion groove 108 with a shallow depth in an inserting direction from the external thread section 106. The pipe body mounting section (cylindrical section for inserting a pipe body) 104 is formed to have an outer diameter and a length which are suitable for a given pipe body 20 as illustrated in FIG. 2 to be fitted and inserted. The length is set to be longer than a total size of a depth of the insertion groove 108 described above and a length of the sleeve 300 to be described below when the external thread section 106 of the joint main body 100 and the internal thread section 202 of the cap nut 200 are screwed. In addition, the external thread section 106 is formed to surround the pipe body mounting section (cylindrical section for inserting a pipe body) 104 on the proximal side through the annular insertion groove 108, in which a relationship between the length of the external thread section 106, the depth of the insertion groove 108, and the length of the ring-shaped elastic member is adjusted so that when the external thread section 106 and the internal thread section 202 are screwed, the end face 300a of the distal end side of the sleeve 300 comes into contact with the one end face 400a of the elastic member 400 in the axial direction in the insertion groove 108 to tightly press the elastic member 400. Further, reference sign 108a represents a groove bottom of the insertion groove 108. In addition, a locking annular groove 100e for preventing the pipe body 20 inserted in the outer circumferential surface on the pipe body mounting section from falling off may be formed in the pipe body mounting section (inserting cylindrical section for inserting a pipe body) 104.

The elastic member 400 is composed of a synthetic resin and, in the present embodiment, as the elastic member 400, silicone rubber having a durometer hardness of 50A is used. Here, relationships between the hardness of the elastic member 400 and compression at two positions (the compression section-1 and the compression section-2) described above are studied. In the present embodiment, the elastic member 400 is made of the silicone rubber having the durometer hardness of 50A and the hardness is lower than that of the joint main body 100 made of metal or the sleeve 300 made of POM which is a relatively hard synthetic resin. In addition, the durometer hardness of a typical pipe body is 70A to 65D; however, in the present embodiment, a rubber hose having the durometer hardness of 73A is used as the pipe body 20, and thus the hardness of the elastic member 400 is lower than the hardness of the pipe body 20. In this manner, since the durometer hardness (50A) of the elastic member 400 is lower than the hardness of the joint main body 100, the sleeve 300, and the pipe body 20, the elastic member 400 is surrounded by a member having higher hardness when the elastic member is pressed and compressed by the sleeve 300, and thus the elastic member has no way to escape. As a result, the elastic member 400 causes the self-repulsion force to function (be applied) in two directions of the axial direction (toward the sleeve 300) of the elastic member and the radial direction of the pipe body 20, and thereby compression at two positions described above is effectively achieved. The elastic member 400 specifically has a durometer hardness of, preferably 40A to 90A, in the axial direction of the sleeve 300, and the more high the hardness, the lower the workability, because torque is increased when the cap nut 200 is fastened. In addition, in the radial direction of the pipe body 20, the hardness is functionable if it is 40A to 60A as the durometer hardness of typical rubbers; however, the present inventors find that the hardness is, most preferably, 40A to 50A. In this manner, in the pipe joint 10 of the present embodiment, since the durometer hardness of the elastic member 400 is 40A to 50A, the repulsion force in the axial direction of the sleeve 300 and in the radial direction of the pipe body 20 is maintained for a long period of time. In addition, since silicone rubber is used for the elastic member 400, the elastic member has high rebound resilience and good in heat resistance. Therefore, the sealability is increased not only at normal temperature, but also at a high temperature. As above, the relationship between the hardness of the elastic member 400 and the hardness of the pipe body 20 or the sleeve 300 is preferably, hardness of the elastic member 400<hardness of the pipe body 20<hardness of the sleeve 300, so as to cause the compression at two positions (the compression section-1 and the compression section-2) described above to efficiently function.

In addition, in the pipe joint 10 of the present embodiment, a further shaping process is performed on the ring-shaped elastic member 400 for the purpose of improvement of workability. In other words, as illustrated in FIG. 6, the upper and lower ends of the substantial ring shape on the outer circumferential surface side and upper and lower ends on the inner circumferential surface side of the elastic member 400 are all chamfered as illustrated by arrows R, respectively. In this manner, the upper and lower ends of the substantial ring shape on the outer circumferential surface side and the upper and lower ends on the inner circumferential surface side of the elastic member 400 are all chamfered. As will be described below, in order to assemble the pipe joint 10 of the present embodiment, the elastic member 400 is inserted and disposed in the insertion groove 108 and then the pipe body 20 is inserted along the chamfered portions in a case where the pipe body 20 is inserted down to a groove bottom 108a of the insertion groove 108. Therefore, the pipe body 20 is easily inserted and the workability is improved. In addition, since the chamfering is performed on both upper and lower side on the outer circumferential surface side and the inner circumferential surface side of the elastic member 400, upper or lower directionality is not formed and thus a product quality is stabilized. In other words, an error in picking the upper and lower sides of the elastic member 400 is not made for each product by a builder during an operation of assembly of the pipe joint 10. Further, the upper and lower ends of the substantial ring shape on the outer circumferential surface side and upper and lower ends on the inner circumferential surface side of the elastic member 400 do not all need to be chamfered. For example, in order to easily insert the pipe body 20 in the insertion groove 108, the chamfering may be performed only on the inner circumferential surface side.

In addition, in the pipe joint 10 of the present embodiment, as illustrated in FIG. 5, in order to improve the workability, the depth of the insertion groove 108 of the joint main body 100 is set to have a size with which the elastic member 400 and the sleeve 300 can be fixed. In other words, since the height of the elastic member 400 is smaller in size than the depth of the insertion groove 108, the sleeve 300 which is disposed on the elastic member 400 in the insertion groove 108 is fixed by the insertion groove 108, and thus the workability during the insertion of the pipe body 20 in the sleeve 300 is improved. In other words, since the sleeve 300 is fixed to the insertion groove 108 and does not move during the insertion of the pipe body 20, the workability in the assembly of the pipe body 20 and the pipe joint 10 is improved. In this manner, in the pipe joint 10 of the present embodiment, the insertion groove 108 is formed to have a depth greater in size than the height of the elastic member 400, and thereby the groove functions as a sleeve fixing groove.

The sleeve 300 is made of a synthetic resin and, as illustrated in FIG. 1 to FIG. 5, is formed from a cylindrically molded body having a smooth inner circumferential surface, and has an inner diameter with which the sleeve 300 can come into sliding contact with the outer circumferential surface of the pipe body 20 in a fitting manner. In the sleeve 300, an annular section 300B having a thin thickness in an intermediate section thereof is formed to have a diameter which can be reduced toward the central axis, a cylindrical section 300A on the front end, which extends from the annular section 300B to the left side in the drawing, is formed to have a thick thickness, and the end face 300a of the distal end side as described above is formed on the front end face of the cylindrical section. In addition, an annular inclined surface (locking end face) 300A1, which engages with a locking protrusion 200T of the cap nut 200, is formed on the outer circumferential edge of the cylindrical section 300A on the rear end side. A cylindrical section 300C on the rear end side, which extends to the right side in the drawing, is formed to have a diameter which can be reduced, similar to the annular section 300B. An annular groove 300CG for mounting the sleeve mounting elastic member 500 is formed on the inner circumferential surface of the cylindrical section 300C on the rear end side. A plurality of streaks of slits (notches) S, which are opened at the rear end edge, are formed at a certain interval on the circumferential surface of the cylindrical sections 300B and 300C (including a section of the annular groove 300CG portion) in the intermediate section and on the rear end side, respectively, which can be reduced in respective diameters, and separated pieces SU, which are divided by the plurality of slits S, are formed to be arranged at a certain interval and to have a cylindrical shape. External pressure (pressing force) is applied to the separated pieces SU from a fitting surface (tapered inner circumferential surface) 200a of the cap nut 200, and thereby the cylindrical sections 300B and 300C in the intermediate section and on the rear end side are reduced in diameter toward the central axis. Further, it is needless to say that the number or a shape of the slits S or the separated pieces SU is not limited to the in the drawing.

When the cap nut 200, to be described below, is fastened to the joint main body 100, the sleeve 300 made of a synthetic resin is reduced in diameter due to the pressing force from the fitting surface (tapered inner circumferential surface) 200a of the cap nut 200, and thereby the outer diameter of the pipe body 20 is uniformly compressed and held. Further, as illustrated in FIG. 4C, R chamfering is performed on the outer diameter portion of the sleeve 300. The sleeve 300 is subjected to the R chamfering and formed of a synthetic resin member, and has a structure in which a plurality of slits S are provided, and thereby a load produced during expansion and compression is reduced such that it is possible to fasten the cap nut 200 with low torque when the cap nut 200 is fastened to the joint main body 100. Particularly, since slit processing, in which a plurality of streaks of slits (notches) S are formed on the circumferential surface of the sleeve 300, is performed, it is possible to fasten the cap nut 200 with the low torque when the sleeve is pressed by the fitting surface 200a of the cap nut 200 and the expansion and compression are performed, because the slits (notches) S are formed at intervals. In addition, the sleeve 300 is uniformly expanded and contracted on the circumference (circumferential surface) of the pipe body 20. In this manner, since the sleeve 300 can be uniformly expanded and compressed on the circumference (circumferential surface) of the pipe body 20, it is possible to be smoothly and uniformly expanded and compressed on the circumference (circumferential surface) of the pipe body 20.

In addition, as described above the sleeve mounting elastic member 500 having substantially the ring shape is mounted in the annular groove of the sleeve 300, the sleeve mounting elastic member 500 is made of NBR, and rebound resilience is significant and heat resistance up to about 100° C. In the pipe joint 10 of the present embodiment, in the compression section-1 described above, since the sleeve 300 compresses the pipe body 20 in the radial direction thereof through the sleeve mounting elastic member 500. Therefore, although outer diameter deformation (compressed permanent distortion) of the pipe body 20 occurs, it is possible to supplement the outer diameter deformation (compressed permanent distortion) with the rebound resilience (repulsion force) of the sleeve mounting elastic member 500 and it is possible to apply compression on the outer diameter of the pipe body 20 for a long period of time.

In the cap nut 200, a front end portion 200A thereof is formed to have a thin thickness and the internal thread section 202, which is screwed to the external thread section 106 of the joint main body 100 described above, is provided on the flat inner circumferential surface parallel to the central axis. The rear end portion 200B is formed to have a thick thickness and has the locking protrusion 200T which protrudes to the inner side so as to accommodate and lock a locking end face 300C1 of the cylindrical section 300C of the sleeve 300 on the rear end side and the locking end face 300A1 of the cylindrical section 300A of the sleeve on the front end side, and the rear end portion 200B forms a inner circumferential surface (corresponding to the fitting surface 200a) which is tapered as close to the rear end side thereof. Further, the outer circumferential surface of the cap nut 200 is formed to have a spanner receiving hexagonal.

Hereinafter, an example of a use of the pipe joint 10 of the present embodiment will be described. Before the pipe body 20 is fitted and inserted in the pipe body mounting section (cylindrical section for inserting a pipe body) 104 of the joint main body 100 which is attached to the cylindrical opening of the medical equipment (not illustrated) by the attaching cylindrical section 100c, the elastic member 400 is inserted and disposed in the insertion groove 108 of the joint main body 100, the sleeve mounting elastic member 500 is mounted in the annular groove 300CG of the sleeve 300, and the cap nut 200 and the sleeve 300 are fitted and mounted in this order from the distal end of the pipe body 20. Further, as illustrated in FIG. 2, the sleeve 300 is accommodated on the inner side of the internal thread section 202 of the cap nut 200 which is fitted on the outer circumferential surface of the pipe body 20, the distal end portion of the pipe body 20 is inserted in the pipe body mounting section (cylindrical section for inserting a pipe body) 104 of the joint main body 100 such that the end face 300a of the distal end side of the sleeve 300 comes into contact with the one end face 400a of the ring-shaped elastic member 400 in the axial direction, and the most distal end portion of the pipe body 20 reaches the groove bottom 108a of the image forming apparatus insertion groove 108. At this time, as illustrated in FIG. 2, the sleeve 300 is disposed in a state of being substantially parallel to both sides of the flat inner circumferential surface of the front end portion 200A of the cap nut 200 and the outer circumferential surface of the pipe body 20, as a whole. In addition, the sleeve mounting elastic member 500 mounted in the annular groove 300CG of the sleeve 300 comes into contact with the outer circumferential surface of the pipe body 20 which is maintained to have a shape as is in a substantially initial state. Further, the locking end face 300c1 of the cylindrical section 300C of the sleeve 300 on the rear end side is locked to the locking protrusion 200T of the cap nut 200.

From this state, the internal thread section 202 is screwed to the external thread section 106 of the joint main body 100 and the cap nut 200 is deep inserted. In other words, the cap nut 200 is caused to move forward in a twisting manner. Depending on the deep insertion, the locking end face 300C of the cylindrical section 300C of the sleeve 300 on the rear end side, which comes into contact with the locking protrusion, is pressed forward by the locking protrusion 200T of the cap nut 200 and the end face 300a of the distal end side of the sleeve 300 starts to press the one end face 400a of the elastic member 400 in the axial direction in the insertion groove 108. Meanwhile, the cap nut 200 is further move forward in the twisting manner, and external pressure (pressing force) is applied from the fitting surface (tapered inner circumferential surface) 200a of the cap nut 200, and thereby the cylindrical sections 300B and 300C in the intermediate section and on the rear end side of the sleeve 300 are reduced in diameter toward the central axis. In this manner, the cylindrical section 300C on the rear end side comes into pressing contact with and interlocks with the outer circumferential surface of the pipe body 20 such that the sealability is not only obtained, but also, the cylindrical section 300C tightly presses the sleeve mounting elastic member 500 mounted in the annular groove 300CG such that good sealability is exhibited. Further, when the cap nut 200 moves forward in the twisting manner and is completely screwed to the external thread section 106 of the joint main body 100, the end face 300a of the distal end side of the sleeve 300 continues to press the one end face 400a of the elastic member 400 in the axial direction in the insertion groove 108 as illustrated in FIG. 3. As a result, the elastic member 400 pushes back the end face 300a of the distal end side of the sleeve 300 with the self-repulsion force, and thereby the compressed elastic member 400 is tightly pressed to come into close contact with the wall surface of the insertion groove 108 and with the outer circumferential surface of the pipe body 20. In this manner, it is possible to further stabilize the self-repulsion force of the elastic member 400 and to cause the self-repulsion force to be applied to the sleeve 300. The entire sleeve 300 is hereby pressed to the rear end portion 200B side of the cap nut 200, the outer circumferential surface of the pipe body 20 is pressed such that the cylindrical section 300C of the sleeve 300 on the rear end side is further reduced in diameter by the reaction force received by the outer circumferential surface 300C2 of the cylindrical section 300C of the sleeve 300 on the rear end side from the fitting surface (tapered inner circumferential surface) 200a of the cap nut 200 with an engagement portion between the inclined surface 300A1 of the cylindrical section 300A of the sleeve 300 on the front end side and the locking protrusion 200T as a support point, and, as a result, the sealability including the sleeve mounting elastic member 500 is further improved. Further. FIG. 3 does not illustrate such a state; however, if the pressing-contact portion of the pipe body is irreversibly deformed by the cylindrical section 300C of the sleeve 300 on the rear end side, the compressed elastic member 400 continues to press, with the self-repulsion force, the end face 300a of the distal end side of the sleeve 300. Therefore, the deformed portion on the outer circumferential surface of the pipe body 20 presses the modified portion of the inner circumferential surface of the pipe body 20 such that the cylindrical section 300C described above is further reduced in diameter and the airtightness (liquid-tightness) with the pipe body 20 is maintained.

With the pipe joint having the same configuration as above as Example 1, and with a pipe joint having a configuration to be described below, which is different from Example 1, as Comparative Example 1, Comparative Example 2, specimens are prepared, respectively, and in order to check the airtightness (liquid-tightness) with the pipe body of the respective pipe joint under a temperature cycling environment, a hot water circulating test, in which the airtightness (liquid-tightness) is checked through a heat cycle through which heated water having a temperature of above and below 20° C. and hot water having a temperature of 92° C. alternately flows, was performed. Specifically, in Example 1, the ring-shaped elastic member 400 disposed in the insertion groove is made of the silicone rubber, and the sleeve mounting elastic member 500 is made of NBR. In Comparative Example 1, there is no member corresponding to the ring-shaped elastic member 400 but there is the sleeve mounting elastic member (rubber). In Comparative Example 2, there is no member corresponding to the ring-shaped elastic member 400 and no member corresponding to the sleeve mounting elastic member (rubber). In the airtight (liquid-tight) test, the defined number of heat cycles was performed and the condition was confirmed in a pressure test in which water pressure of 1 MPa was maintained for five minutes and leakage was checked. In the results of the hot water circulating test, in Comparative Example 2 (without neither an elastic member corresponding to the ring-shaped elastic member 400 nor an elastic member corresponding to the sleeve mounting elastic member (rubber)), it was only possible to maintain the airtightness (liquid-tightness) to 100 cycles. In addition, in Comparative Example 1 (without an elastic member corresponding to the ring-shaped elastic member 400, but with an elastic member corresponding to the sleeve mounting elastic member (rubber)), improvement is further performed compared to Comparative Example 2; however, the airtightness (liquid-tightness) is maintained to 150 cycles to 200 cycles as a limit. In comparison, in Example 1, it is possible to maintain the airtightness (liquid-tightness) although exceeding 1300 cycles (further, in a continued test, 1500 cycles are checked). Accordingly, it is understood that significantly good durability is provided even under a hot cycle environment, compared to Comparative Example 1 and Comparative Example 2.

As above, according to the pipe joint 10 of the present embodiment, the elastic member 400 having substantially the ring shape, which corresponds to the end face 300a of the distal end side of the sleeve 300, is disposed in the insertion groove 108 provided at a portion in which the distal end of the pipe body 20 of the joint main body 100 is inserted, the pipe body 20 is mounted, and then the elastic member 400 presses, with the self-repulsion force of the elastic member, the end face 300a of the distal end side of the sleeve 300 in the axial direction. In this manner, the inner circumferential surface 300b of the proximal end side of the sleeve 300 compresses the pipe body 20 in the radial direction, and thereby it is possible to obtain high sealability and to maintain sufficient airtightness (liquid-tightness) even in a case of use, due to a structure, under a severe temperature cycle environment of a temperature of approximately 100° C. from normal temperature. In addition, the sleeve 300 includes a plurality of notches 300c extending from one end portion in the axial direction. When the external thread section 106 of the joint main body 100 and the internal thread section 202 of the cap nut 200 are screwed, the intervals between the notches 300c are narrowed and the sleeve 300 is reduced in diameter. Accordingly, since the inner circumferential surface 300b of the proximal end side of the sleeve 300 compresses the pipe body 20 in the radial direction, high sealability is obtained. Further, an annular groove is formed in the inner circumferential surface 300b of the proximal end side of the sleeve 300, the sleeve mounting elastic member 500 having substantially the ring shape is mounted in the groove, and the inner circumferential surface 300b of the proximal end side of the sleeve 300 compresses the pipe body 20 in the radial direction through the sleeve mounting elastic member 500. In this manner, the sleeve mounting elastic member 500 is disposed, in addition to the elastic member 400, it is possible to improve the sealability.

Further, in the embodiment described above, the joint main body and the cap nut are made of metal and the sleeve is made of a synthetic resin; however, all the components of the pipe joint including the joint main body and the cap nut may be made of a synthetic resin, and a material of a component of the pipe joint is not limited such as the sleeve made of metal, which can be reduced in diameter due to a plurality of notches. In addition, the sleeve may also not have the notches. Further, in the embodiment described above, the elastic member disposed in the insertion groove is composed of a ring-shaped silicone rubber (synthetic resin); however, on the one hand, it is needless to say that another synthetic resin other than the silicone rubber may be used, and the shape is not limited to the ring-shaped one. The elastic member or the like, which is divided into a plurality of arch-shaped rubber pieces and is formed to have a substantial ring shape as a whole, is considered. Here, since it is considered that the synthetic resin, for example, a thermoplastic elastomer, or the like, is plastically deformed under the heat cycle environment and does not even exhibit a function of compression, it is preferable that a synthetic resin without having thermoplasticity in a case where the use under the temperature cycle environment is predicted, similar to the embodiment described above.

Further, in the embodiment described above, the present invention is applied to the joint through which medical equipment and a pipe body are connected; however, the present invention can achieve significant effects in a joint or the like, through which food-related equipment and a pipe body are connected, including a joint which is positioned under a temperature cycle environment of both heating and cooling in a use in which maintenance such as hot water disinfection or the like is considered, and also a joint or the like which connects a pipe which is continuously used under a hot temperature (hot water) without maintenance. In addition, the present invention is not limited to a case in which the pipe body and equipment are connected, but it is needless to say that the invention may be applied a joint between a pipe body and another pipe body.

INDUSTRIAL APPLICABILITY

The present invention is applicable not only to a joint between the medical equipment and the pipe body, but also to every joint of pipe body for every use.

REFERENCE SIGNS LIST 10 pipe joint
20 pipe body
20A distal end (of pipe body)
100 joint main body
104 pipe body mounting section
106 external thread section
108 insertion groove
200 cap nut
202 internal thread section
300 sleeve
300a end face of distal end side
300b inner circumferential surface of proximal end side
400 elastic member
400a one end face (of elastic member) in axial direction
500 sleeve mounting elastic member

The invention claimed is:
1. A pipe joint comprising:
a joint main body that has a flow path inside thereof and that comprises a pipe body mounting section on an outer side of which a pipe body having substantially a cylindrical shape is mounted and an external thread section;
a cap nut having an inner circumferential surface including an internal thread section which is screwed to the external thread section of the joint main body; and
a sleeve having substantially a cylindrical shape having an outer diameter with which the sleeve comes into sliding contact with the inner circumferential surface of the cap nut,
wherein the pipe joint further comprises:
an insertion groove which is formed between the pipe body mounting section and the external thread section of the joint main body and in which a distal end of the pipe body is inserted; and
an elastic member which is disposed in the insertion groove and which comprises a synthetic resin formed to have substantially a ring shape corresponding to an end face of a distal end side of the sleeve, and
wherein in response to the external thread section of the joint main body and the internal thread section of the cap nut being screwed, the end face of the distal end side of the sleeve comes into contact with one end face of the elastic member in an axial direction thereof to compress the elastic member, and the elastic member presses, with a self-repulsion force, the end face of the distal end side of the sleeve in the axial direction, so that an inner circumferential surface of a proximal end side of the sleeve compresses the pipe body in a radial direction of the pipe body through a reaction force received from a fitting surface of the cap nut, and the elastic member itself compresses the pipe body in the radial direction of the pipe body.

2. The pipe joint according to claim 1, wherein a durometer hardness of the elastic member is 40A to 50A.

3. The pipe joint according to claim 2,
wherein the sleeve includes at least one notch extending from one end portion in the axial direction.

4. The pipe joint according to claim 2, further comprising:
a sleeve mounting elastic member having substantially a ring shape, which is mounted on the inner circumferential surface of the proximal end side of the sleeve,
wherein the inner circumferential surface of the proximal end side of the sleeve compresses the pipe body in the radial direction of the pipe body through the sleeve mounting elastic member.

5. The pipe joint according to claim 4,
wherein the sleeve includes at least one notch extending from one end portion in the axial direction.

6. The pipe joint according to claim 1, further comprising:
a sleeve mounting elastic member having substantially a ring shape, which is mounted on the inner circumferential surface of the proximal end side of the sleeve,
wherein the inner circumferential surface of the proximal end side of the sleeve compresses the pipe body in the radial direction of the pipe body through the sleeve mounting elastic member.

7. The pipe joint according to claim 1,
wherein the sleeve includes at least one notch extending from one end portion in the axial direction.

* * * * *